US005624913A

United States Patent [19]

Proctor et al.

[11] Patent Number: 5,624,913
[45] Date of Patent: *Apr. 29, 1997

[54] METHOD REDUCING TNF-ALPHA IN MAMMALS WITH CEREBRAL MALARIA

[75] Inventors: Richard A. Proctor, Madison; Paul J. Bertics, Fitchburg, both of Wis.

[73] Assignee: Wisconsin Alumni Research Foundation, Madison, Wis.

[*] Notice: The term of this patent shall not extend beyond the expiration date of Pat. No. 5,492,899.

[21] Appl. No.: 298,254

[22] Filed: Aug. 30, 1994

Related U.S. Application Data

[63] Continuation-in-part of Ser. No. 137,326, Oct. 15, 1993, Pat. No. 5,492,898, and Ser. No. 137,685, Oct. 15, 1993, Pat. No. 5,516,762, each is a continuation-in-part of Ser. No.976,659, Nov. 16, 1992, abandoned, which is a continuation of Ser. No. 681,036, Apr. 5, 1991, abandoned.

[51] Int. Cl.$^6$ .................. A61K 31/70; C07H 19/167; C07H 19/20
[52] U.S. Cl. .................. 514/47; 514/895; 536/26.23; 536/26.26; 536/27.63
[58] Field of Search .................. 536/27.63, 26.26, 536/26.23; 514/46, 895, 47

[56] References Cited

U.S. PATENT DOCUMENTS

| | | | |
|---|---|---|---|
| 3,678,162 | 7/1972 | Maguire et al. | 424/180 |
| 3,752,805 | 8/1973 | Maguire et al. | 260/211.5 R |
| 3,860,706 | 1/1975 | Ikeda et al. | 424/180 |
| 4,826,823 | 5/1989 | Cook et al. | 514/46 |
| 4,918,061 | 4/1990 | Raetz et al. | 514/62 |
| 5,106,837 | 4/1992 | Carson et al. | 514/46 |
| 5,310,732 | 5/1994 | Carson et al. | 514/46 |

OTHER PUBLICATIONS

Tanke, et al. Abstract summarizing a poster presentation at the 1989 ASCB meeting, p. 17.
Tanke, et al. Abstract, 30th ICAAC meeting, Atlanta, Georgia, Oct. 1990, p. XIX.
Tanke, et al. article titled "Lipid X inhibition of bacterial lipopolysaccharide–stimulated GTP–ase activity", *Cellular and Molecular Aspects of endotoxin reactions*, A. Nowotny et al., Editors, pp. 227–237 (1990).
Lehninger, Albert. Biochemistry: The Molecular Basis of Cell Structure and Function; Second Edition, Worth Publishers, Inc. (New York), p. 730.
Sigma Chemical Catalog, 1992, pp. 676–677.
Gough, et al. article, "Three New Adenosine Triphosphate Analogs: Synthesis and Effects on Isolated Gut", *Journal of Medicinal Chemistry*, 1973, vol. 16, No. 10, pp. 1188–1190.
Proctor, et al. article, "Protection of mice from endotoxic death by 2–methylthio–ATP", *Proc. Natl. Acad. Sci. USA*, vol. 91, pp. 601–6020, Jun. 1994 Microbiology.

*Primary Examiner*—Gary L. Kunz
*Attorney, Agent, or Firm*—Quarles & Brady

[57] ABSTRACT

A method for reducing the TNF-alpha in mammals with cerebral malaria comprising the administration of 2-methylthio-ATP or 2-chloro-ATP.

5 Claims, No Drawings

METHOD REDUCING TNF-ALPHA IN MAMMALS WITH CEREBRAL MALARIA

This invention was made with United States government support awarded by NIH, Grant #AI 1210. The United States Government has certain rights in this invention.

RELATED CASE

The present application is a continuation-in-part of U.S. patent application Ser. No. 08/137,326, filed Oct. 15, 1993, now U.S. Pat. No. 5,492,898, and Ser. No. 08/137,685, filed Oct. 15, 1993, now U.S. Pat. No. 5,516,762, which are continuation-in-part of Ser. No. 07/976,659, filed Nov. 16, 1992, now abandoned, which is a File Wrapper Continuation of Ser. No. 07/681,036, filed Apr. 5, 1991, now abandoned.

FIELD OF THE INVENTION

The present invention generally relates to the treatment of diseases. More particularly, it relates to methods of treating cerebral malaria and other diseases in which tissue necrosis factor (TNF-α) is produced by disease causing agents.

BACKGROUND OF THE INVENTION

It is generally believed that there are a number of animal diseases in which the disease promoting organism causes an interaction between macrophages and T-cells (lymphocytes) to induce the production of tissue necrosis factor (TNF-α) which can have serious adverse effects upon the animal. Among such diseases are cerebral malaria, endotoxin shock, toxic shock syndrome, streptococcal toxic shock syndrome, respiratory failure caused by mycoplasma super antigen, staphylococcus enterotoxin diseases, and diseases caused by parasitic super antigens or viral super antigens.

The human disease malaria, particularly malaria caused by *Plasmodium falciparum*, remains a serious medical challenge. It afflicts over 200 million people and in Africa alone is responsible for over one million deaths among children each year. Cerebral malaria is a most severe and frequently fatal consequence of falciparum malaria in the young and non-immune. Cerebral malaria causes acute symptoms including leaky blood vessels in the brain and cerebral edema. Antimalarial chemotherapy initiated at the time of cerebral symptoms often fails to alter the fatal outcome, and mortality even with the best current therapies ranges from 10 to 50%. The pathological processes responsible for the cerebral manifestations are not well understood. Cerebral tissue obtained post-mortem reveals grossly congested cerebral vessels, occluded with infected red blood cells adherent to the endothelium, which leads to the subsequent encephalopathy secondary to cerebral anoxia.

An immunopathological component to the cerebral manifestations has been suggested from several studies which have implicated a role for tumor necrosis factor (TNF). The malaria disease causing agent causes activation of T-cells (CD4 and possibly CD8) and macrophages which release the cytokines TNF-α, IL-1 and IL-6 which lead to increased vascular permeability and cerebral edema. In the murine model of cerebral malaria, the immunopathological role of TNF has been most thoroughly studied. It has been observed that cerebral pathology and mortality have been abrogated by concurrent treatment with antibodies against cytokines associated with cell activation and TNF production and specifically with anti-TNF antibodies[1,2,3]. It is important to note that some of the pathological processes in the murine model are similar to those in human cerebral malaria, e.g., the underlying mechanism of vascular occlusion is closely paralleled[4,5,6]. Typically in the murine model, CBA/ca mice are infected with *Plasmodium berghei* ANKA strain and within 6-15 days 50% or more will expire with cerebral manifestations, primarily ataxia, paralysis and convulsions. Histopathology reveals grossly occluded cerebral vasculature[7].

In keeping with the importance of TNF in human cerebral malaria pathology, two case reports have described remarkable recovery from cerebral malaria when antimalarial therapy is combined with phosphodiesterase inhibitors that inhibit TNF synthesis[8,9]. Amelioration of cerebral manifestations and mortality has also been accomplished in the murine CM model with the methylxanthine pentoxifylline and the prostacyclin analog Illoprost without antimalarial treatment[10,11].

In addition to cerebral malaria, gram-negative septic shock, which is characterized by a high mortality rate and is responsible for hundreds of thousands of deaths annually, appears to involve the production of excess TNF-α which results from a cascade of events triggered by the action of bacterial endotoxin which is a lipopolysaccharide (LPS).

Of particular importance concerning the lethal effects of LPS is the observation that nanogram quantities of LPS can induce the release of mediators such as tumor necrosis factor-α, (TNF-α) interleukin-1 (IL-1), and interleukin-6 (IL-6). The release of mediators such as tumor necrosis factor-α (TNF), interleukin-1 (IL-1), and interleukin-6 (IL-6) is thought to produce the toxicity associated with endotoxemia. However, despite the high mortality rate of endotoxic shock, relatively little is known about the biochemical and cellular mechanisms involved in LPS-induced events, e.g., TNF and IL-1 release, although an amplification system is suggested given that nanogram quantities of LPS can produce severe toxicity in animals. Most amplification pathways involve receptors and various enzyme cascades, thus allowing for several points of antagonism within the system. Although certain steps in LPS action are known, such as the stimulation of phosphoinositide hydrolysis, a transient increase in intracellular $Ca^{++}$ levels, and the activation of protein kinase C and phospholipase $A_2$, the lack of specific information on the cellular mechanisms involved in LPS action has impeded the development of therapeutic agents for preventing endotoxin shock.

Macrophages are particularly important cells in LPS-mediated TNF-α, IL-1, and IL-6 release. Although a detailed understanding of the cellular and biochemical processes through which LPS activates macrophages is unknown several lines of indirect evidence suggest that G-proteins might be involved in LPS action, which would be consistent with a receptor-linked cellular amplification pathway. Our earlier finding that LPS stimulates a macrophage membrane-associated GTPase, an activity that is a hallmark of G-protein involvement, further supports a role for G-proteins in endotoxicity.

Obviously, it would be advantageous to have agents and methods to prevent disease causing agents, such as the malaria parasite and LPS, from producing tumor necrosis factor (TNF).

BRIEF SUMMARY OF THE INVENTION

It is an object of the present invention to disclose compounds which are useful in methods to prevent disease agents, such as the malaria parasite or LPS, from interacting with macrophages and T-cells to produce excess tissue necrosis factor (TNF-α).

It also is an object to disclose methods of treatment of mammals to protect them from the deleterious effects of malaria and other diseases which produce excess TNF.

The compounds which are useful in the method of the present invention may be represented by the following formula:

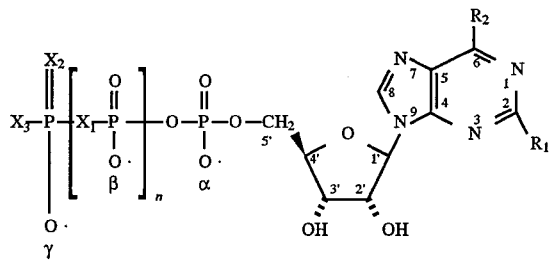

in which $X_1$ is a hydroxylation preventing group, such as —O—, —NH— or —$CH_2$—; $X_2$ is =O or =S; $X_3$ is —OH or —F; $R_1$ is selected from an electron withdrawing group such as a thioalkyl containing 1 to 4 carbon atoms or a halogen or halogen-containing group, such as Cl- or F- or $CCl_3$-; $R_2$ is —H, —CL, —F, —OH, =O, lower alkyl of 1 to 4 carbon atoms, —$NH_2$, —$NH(CH_3)$, —$N(lower alkyl)_2$, —$NHCOOCH_3$, =S, —SH, —$SCH_3$ or —$SO_3$—; and n is 0 or 1. When n is 0, the compounds are diphosphates.

The methods of treatment of the present invention comprise administering to mammals safe and effective amounts of compounds of Formula I to protect them from the deleterious effects of the malaria parasite and other disease agents which interact with macrophages and/or T-cells to produce TNF-α.

The foregoing and other objects and advantages of the present invention will be apparent to those skilled in the art from the description of the preferred embodiment.

In the preferred practice of the present invention, a compound of Formula I is administered to an animal in a safe and effective amount to inhibit the release of TNF-α and IL-1 by a disease causing agent, such as the maleria parasite. The preferred compounds are 2-methylthio-ATP (2-MeS-ATP) and 2-chloro-ATP (2-Cl-ATP) and the preferred route of administration is intravenously.

Representative of other compounds that may be used in the methods are the following:
2-methylthio-ADP
2-chloro-ADP
2-methylthio-adenosine 5'-[β,8-imido]-triphosphate (2-MeS-AMPPNP)
2-methylthio-adenosine 5'-[β,8-methylene]-triphosphate (2-MeS-AMPP-$CH_2$-P)
2-chloro-adenosine 5'-[β,8-imido]-triphosphate (2-Cl-AMPPNP)
2-chloro-adenosine 5'-[β,8-methylene]-triphosphate (2-Cl-AMPP-$CH_2$-P)

We first discovered that 2-methylthio-ATP and 2-chloro-ATP are useful for inhibiting the release of TNF-α and IL-1 or preventing the production and lethal effects of TNF-α and IL-1 as a result of studying LPS-stimulated GTPase activity. During the course of studying LPS-stimulated GTPase activity, we first made the unexpected observation that ATP greatly enhanced the LPS-stimulation of macrophage membrane GTPase activity. Because ATP is an agonist for several purine nucleotide receptors that are present on the surface of macrophages and other cell types and that are coupled to G-proteins, and because ATP is released from the adrenal gland and other cells during inflammation, we initiated several studies to examine the possible linkage of cell surface macrophage purinoreceptors to the LPS-responsive GTPase activity and to LPS-induced death.

To define more clearly the relationship between adenine nucleotides and LPS, the activity of various purines was tested in the GTPase assay of our earlier application using macrophage membranes. Although ATP, ATPTS, ADP, and AMPPNP caused modest to little activation of GTPase activity in the absence of LPS, and LPS alone induced only a small activation of GTPase activity, the addition of LPS together with these purines triggered a synergistic increase (3–7-fold) in GTPase activity. The stimulation of basal GTPase activity by low levels of ATP and ADP suggested the presence of G-protein coupled purinoreceptors in these membranes. In addition, the activity of ATPγS and AMMP-PNP further supported the action of purinoreceptors over a phosphoryl donor activity, as these ATP analogs are poorly or non-hydrolyzable. The inhibition of GTPase at very high levels of ATP and ADP is likely to be due to competitive inhibition versus GTP for the GTPase. In contrast to ADP and the ATP analogs, the compounds, adenosine, AMP, NAD and theophylline failed to stimulate basal GTPase activity or synergize with LPS.

We discovered that both 2-methylthio-ATP (2-MeS-ATP) and 2-chloro-ATP (2-Cl-ATP) enhance the basal GTPase activity, but not the LPS-stimulated GTPase activity.

While these in vitro results were provocative, the antagonistic activity of these compounds needed to be assessed in an in vivo model of endotoxemia. In this regard, it was found that the lethal effects of endotoxin in mice were blocked by both 2-MeS-ATP and 2-Cl-ATP.

The experimental work and examples described hereafter demonstrate the usefulness of the method of the present invention in treating diseases, such as malaria and endotoxin shock, in which TNF-α is produced by action of a disease agent.

Experimental Work

Materials and Methods
Animals
6 week old, female CBA/Ca mice (Jackson) were infected from a source mouse by intraperitoneal injection, with $10^6$ parasitized erythrocytes of the *Plasmodium berghei* ANKA strain. Mice were given food and water al libitum. Parasitemias were determined by Giemsa-stained thin blood films.

EXAMPLE 1

Cerebral Malaria Experiments

Three experiments with two groups, control and treated, with six mice per group were completed. Treatment groups included each mouse receiving one I.V. injection of 0.1 mg MethylthioATP (RBI) in 100 ul saline beginning approximately 0.5–1 hour after infection and every day following through day 10. Each injection required brief anesthesia of the mice with ether. Control mice received the same treatment and injections with 100 ul of saline only. Survival time and signs of CM (ataxia, seizure and paralysis) were recorded.
Results The in vivo data showed a statistically significant survival rate of 17 out of 20 mice in the 2-MeS-ATP treated group (versus only 8 out of 20 controls). Equal groups of CBA/Ca mice infected with *P. berghei* ANKA were injected intravenously with saline or 0.1 mg per mouse per day for 10 days beginning on the day of infection. Despite the daily anaesthesia and injection, there were no adverse effects or changes in the course of malaria and mortality of this treatment as compared to infected but non-injected mice. Total mortality by day 12 was 12 of 20(%) for controls and 3 out of 18(%) for the 2-MeS-ATP treatment group. All the surviving mice died by week 4–5 of overwhelming parasitemia (in excess of 60%) and severe anemia. Parasitemia was not significantly different from controls. Prior to signs and mortality on day 6 parasitemia was (6.64%) in untreated controls versus (6.81%) for the 2-MeS-ATP groups and following cerebral mortality on day 12 the parasitemia was (18.16%) for control versus (19.6%) for the 2-MeS-ATP groups.

EXAMPLE 2

GTPase Assay

The preferred assay is comparable to that described by Cassel et al., Biochem, Biophys. Acta 452, 538–551 (1976), and Neer et al., J. Biol. Chem. 259, 14222–14229 (1984), with two main exceptions: (1) We add ammonium sulfate because we found that although 300 µg LPS/ml increased GTPase activity by ~30% in the absence of ammonium sulfate, in the presence of an optimal amount of ammonium sulfate (250 mM), the LPS-induced GTPase activity was nearly 3-fold above the reduced basal rate. Under these conditions, GTPase activation was evident at 100 µg LPS/ml (roughly 6 µM assuming an average MW~17,000 kDa), and the maximal effect was seen by 300 µg/ml LPS. (2) To show adenosine nucleotide synergism with LPS-stimulated GTPase activity, either 10 µM ATP or 30 µM ADP replace the 0.1 mM ATP and 0.2 mM AMPPNP of the standard assay described by Cassel et al. and Neer et al.

In the assay, a candidate compound (0.001–1000 µM) is dissolved or suspended in 100 µl of a reaction buffer containing 20 mM HEPES (pH 7.4), 0.01 mM ATP or 0.03 mM ADP, membranes isolated from RAW 264.7 cells, 2 µM $\gamma$-$^{32}$P-GTP (3–9×10$^3$ cpm/pmol), 5 mM MgCl$_2$, 18 µM LPS (based on an estimated MW of 17,000 kDa for E. coli 0111:B4 endotoxin), and 250 mM ammonium sulfate. The reaction is initiated by the addition of the $\gamma$-$^{32}$P-GTP and the mixture incubated at 30°–37° C. for 15 to 30 minutes. The reaction is terminated by the addition of 500 µl of 5% trichloroacetic acid and 500 µl of 0.1 gm/ml acid-activated charcoal in 5% trichloroacetic acid. The samples are centrifuged at 14,000×g for 10 minutes, and a 550 µl aliquot of the supernatant is removed for scintillation counting. The supernatant will contain the released $^{32}$Pi. The extent of GTPase inhibition is measured by the decrease in the amount of $^{32}$Pi released from $\gamma$-$^{32}$P-GTP. Appropriate controls include mixtures with one of the following omitted: (i) test compound, (ii) endotoxin, and (iii) ATP, ADP or AMPPNP.

The macrophage-like murine cell line RAW 264.7 is cultured using RPMI 1640 medium supplemented with 10% fetal calf serum (FCS) containing <0.1 ng/ml LPS. The membranes are resuspended in 20 mM HEPES (pH 7.4), 1 mM dithiothreitol, 1 mM EDTA and 10 µg leupeptin/ml. Aliquots are stored at −70° C. until assayed.

Effect of ATP

To further characterize the specificity of the LPS-stimulated GTPase, we first assayed its activity in the absence of any other nucleotides, and then compared this response to that found in reactions containing various ATPase/nucleotidase inhibitors. If the GTPase activity is due to a generalized increase in nucleotidase-like activities, one would expect that the inclusion of these inhibitors would attenuate the LPS-stimulated activity. Release of $^{32}$Pi from $\gamma$-$^{32}$P-GTP would be predicted to be unaffected or even enhanced (more non-specific substrate hydrolysis) in the absence of these agents. Surprisingly, we observed that in the absence of any added adenine nucleotides, there was very little detectable LPS-enhanced GTPase activity in the macrophage membranes. However, when either ATP, ADP or the non-hydrolyzable ATP analog AMPPNP was included in the incubation, there was a pronounced increase in LPS-stimulated GTPase activity. Moreover, the addition of the ATPase inhibitors ouabain, bafilomycin and N-ethylmaleimide did not block LPS-stimulated GTPase activity in the presence of ADP. Conversely, as expected, the very general phosphoryl transferase inhibitor, sodium orthovanadate, did block LPS activation.

Because the above inhibitor studies indicated a maximum LPS-stimulated GTPase activity in the presence of ATP and ATP analogs, we investigated this interaction by measuring the ATP-dependence of the GTPase activity in macrophage membranes in the presence and absence of an optimal dose of LPS. ATP alone exhibited a biphasic stimulation of GTPase activity, with the maximum effect being observed around 1–10 µM. This stimulation by ATP may be due to the action of purinoreceptors, i.e., the cell surface adenosine and ATP receptors which are well-characterized to be coupled to various G-proteins.

When ATP and LPS are added together, there is a striking stimulation of GTPase activity at 1–10 µM ATP which is much greater than that seen with ATP or LPS alone. This synergistic stimulation by ATP plus LPS is also biphasic, with the inhibition of GTPase activity observed at very high ATP levels probably resulting from competitive or ionic effects. These data suggest that LPS may interact in some fashion with the purinoreceptor signal transduction pathway and that the LPS-mediated GTPase activation is not the result of a non-specific ATPase or other nucleotidase activity.

To assess whether the LPS/ATP-enhanced GTPase is a "low $K_m$" form, which would be expected for a variety of large and small MW G-proteins, as well as for various GAP and ARF-like proteins, as opposed to a "high $K_m$" form, such as a phosphatase, we assayed the GTPase activity using 0.2 and 50 µM GTP essentially as described previously. In view of the interactive effects of LPS and ATP, we measured high and low $K_m$ GTPase in the absence of added ATP, as well as in the presence of a maximal activating dose of ATP (10 µM), and compared these results to those obtained using our standard assay conditions (2 µM GTP, 0.1 mM ATP, 0.2 mM AMPPNP). The LPS and ATP stimulated a low $K_m$ GTPase activity by ~30% and 70%, respectively, when added individually. This stimulation of low $K_m$ activity was slightly greater than that estimated using the standard assay conditions. In addition, the combined effects of LPS and ATP on GTPase activity also appeared to represent an influence on a low $K_m$ component, with the stimulation calculated for the low $K_m$ activity (228% of basal activity) being comparable to the stimulation (208% of basal activity) measured using our standard assay conditions. In sum, the LPS-stimulated GTPase activity appears specific for GTP, it exhibits a low $K_m$ (GTP), and it is insensitive to various ATPase inhibitors. The LPS stimulation of GTPase activity is enhanced by adenine nucleotides.

Effect of ATP Analogs

In the presence of LPS, ATP results in a three-fold increase in activity of the GTPase. Therefore, we examined the ability of ATP analogs to stimulate LPS-enhanced GTPase activity. In dose-response studies, the relative abilities of purines to stimulate LPS-enhanced GTPase were: ATP> ATPγS> ADP> AMPPNP>> β,γ methylene ATP> 2-Cl-ATP> 2-MeS-ATP.

AMP and adenosine at 100 µM were ineffective, while ATP was active at 1 µM. This is the general order of purine agonist activity for the P2-type purinoreceptor (P2-R). Also, IBMX, an antagonist of both types of P1 purinoreceptors, but with no effect on P2 receptors, did not alter the LPS activation of the GTPase. (There are no known P2x, P2y, or P2z receptor antagonists currently available, while ATP is a P2t inhibitor, but an agonist in our system.) Of interest, one of the Gi-like proteins linked to the P2-purinoreceptors is resistant to pertussis toxin inactivation which is consistent with our results. Also, P2-receptor activation is linked to inositol phosphate breakdown in HL60 cells which is an event also associated with LPS action. Finally, LPS has been reported to decrease purine exonucleotidase activity of glomerular endothelial cells, as assessed by enzyme cytochemistry. These results open the possibility that the P2-R may be involved is some LPS-mediated activities. For example, since ATP infusion is known to result in shock, one might hypothesize the following events: LPS sensitizes P2-R to ATP via enhanced ligand binding to the P2-R or increased G-protein interaction with P2-R, and LPS decreases intravascular breakdown ATP and ADP. Thus, in the presence of LPS, normal concentrations of ATP could result in shock and death.

Examination of the dose-response curves of ATP and ATP analogs show that 2-chloro-ATP (2-Cl-ATP) and 2-methylthio ATP (2-MeS-ATP) have no stimulatory effect on LPS-induced GTPase activity. Because they both are excellent ligands for two of the subtypes of the P2-R (P2y- and P2z-receptors), we hypothesized that these compounds might be antagonists. We found that both of them did antagonize the stimulatory effects of ATP on LPS-inducible GTPase activity. When increasing amounts of either of these compounds (0–100 µM) were added to the macrophage assay system, the activity of the LPS-enhanced GTPase decreased substantially.

EXAMPLE 3

2-MeS-ATP Protection of Mice From TNF-α Produced by a Lethal Endotoxin-Challenge C57Bl/6 mice (2–3 months old, 25–35 g) were ether-anesthestized and injected retroorbitally with 0, 800 µg, or 900 µg LPS (*E. coli* 0111:B4, Sigma, St. Louis, Mo.) followed within one minute by a contralateral retroorbital injection of 0–1300 µg 2-MeS-ATP; both compounds were injected using a saline vehicle. The data represent the number of animals surviving at 48 hours. The experiment was terminated after 72 hrs, and only two animals (asterisks) died after 48 hrs (one in Experiment 1 and one in Experiment 2). Statistical comparisons between the 2-MeS-ATP treated animal groups and the control group (animals not receiving 2-MeS-ATP) were performed using the unpaired Student's t test. The p values are shown below the total for those groups exhibiting significant (p<0.01) differences.

| Experiment | LPS (µg) | Mortality (# Alive/Total) 2-MeS—ATP Dose (mg/Mouse) | | | |
|---|---|---|---|---|---|
| 1 | 800 | 4/10 | 3/6 | 6/6 | 10/10* |
| 2 | 800 | 0/10 | 0/10 | 3/10* | 10/10 |
| 3 | 900 | 0/10 | — | — | 9/10 |
| 4 | 900 | 1/12 | — | — | 15/16 |
| 5 | 900 | 0/6 | — | — | 5/6 |
| Total: | | 5/48 | 3/16 | 9/16 | 49/52 |

(p < .001) (p < .00001)

EXAMPLE 4

Survival of Mice After Injection of LPS and a Second Injection of 2-Methylthio-ATP All animals were given an initial injection of 600 µg LPS. Compounds given as a second injection were dissolved in saline solution. Average weight of mice was 19.5 g.

| Second Injection | Number of Mice Surviving After 72 Hours |
|---|---|
| Saline | 0/6 (0%) |
| 10 µg 2-methylthio-ATP | 3/5 (60%) |
| 100 µg 2-methylthio-ATP | 3/4 (75%) |
| 1 mg 2-methylthio-ATP | 3/6 (50%) |

The 2-MeS-ATP decreased the amount of TNF-α cytotoxic activity in a culture supernatant after treatment with LPS (12). It also was found in an in vivo model of endotoxemia in mice that, 2-MeS-ATP decreased the serum concentrations of TNF-α at 1 hour and of IL-1 at 4 hours (13). The effects of 2-MeS-ATP were immunomodulatory, rather than immunosuppressive, because the 2-MeS-ATP did not block IL-6 release also measured at 4 hours. Thus, 2-MeS-ATP inhibited the release of specific mediators and was not simply a cytotoxic agent.

EXAMPLE 5

Survival of Mice After Injection of LPS and a Second Injection of 2-Chloro-ATP

All animals were given an initial injection of 600 µg LPS. The 2-chloro-ATP given as the second injection was dissolved in saline solution. Average weight of mice was 19.5 g.

| Second Injection | Number of Mice Surviving After 72 Hours |
|---|---|
| Saline | 0/6 (0%) |
| 10 µg 2-chloro-ATP | 4/6 (67%) |
| 100 µg 2-chloro-ATP | 5/6 (83%) |
| 1 mg 2-chloro-ATP | 1/6 (17%) |

The data of Examples 4 and 5 suggest that purinoreceptors are involved in modulating the release of mediators, such as TNF-α during endotoxemia. This hypothesis also is supported by the observation that ATP and other purines are released from host cells during inflammation. In terms of the mechanism of interaction between LPS and purine nucleotides, several points along a signal transduction pathway are possible. For example, LPS might interact with a purinoreceptor(s) directly, with the G-protein(s) that is linked to a specific purinoreceptor(s), or with regulatory proteins that alter G-protein or receptor function. The concept that LPS interacts with a G-protein directly has theoretical support from the known binding of other lipids to G-proteins. Moreover, if LPS is internalized and acts by association with an intracellular protein (such as a G-protein), then the various macrophage surface proteins that bind LPS may act as transporters. This would explain the necessity for these binding proteins in LPS action, and why cells without an LPS transporter, which could not concentrate LPS intracellularly, would not be LPS responsive.

It remains to be determined if 2-MeS-ATP and 2-Cl-ATP act by competitive inhibition versus active purines such as ADP and ATP, or whether they modulate a specific ATP/ADP purinoreceptor by a separate class of purinoreceptor, or if they stimulate a negative regulatory pathway for TNF-α and IL-1 release. Ultimately, the purification of the components in the LPS-stimulated adenine nucleotide-regulated GTPase activity will be required to define the mechanism more clearly.

The alkylthio compounds represented by Formula I may be prepared by known chemical procedures. For example, a method of introducing a 2-loweralkylthio group into the adenosine molecule is disclosed in the Maguire et al. U.S. Pat. No. 3,752,805; a method of preparing the triphosphates is disclosed in Moffatt, *Canadian Journal of Chemistry*, Vol. 42 (1964), pp. 599 to 604; and methods of effecting ring nitrogen substitution, substitution at exocyclic groups, making modified phosphate groups, synthesizing phosphate esters and synthesizing nucleoside polyphosphates are disclosed by Scheit in his text *Nucleotide Analogs*, a Wiley-Interscience Publication, John Wiley and Sons.

The halosubstituted compounds represented by Formula I may be prepared by known chemical procedures. For example, a method of preparing the 2-chloro derivatives is disclosed in Gough et al., *Journal of Medicinal Chemistry*, 1973, Vol. 6, No. 10, pages 1188-1190; a method of preparing the 2-fluoro derivatives is disclosed in Baldo et al., *Canadian J. Biochem*, Cell. Biol., Vol. 61, 1983, pp. 115-119; a method of preparing the triphosphates is disclosed in Moffatt, *Canadian Journal of Chemistry*, Vol. 42 (1964), pp. 599 to 604; and methods of effecting ring nitrogen substitution, substitution at exocyclic groups, making modified phosphate groups, synthesizing phosphate esters and synthesizing nucleoside polyphosphates are disclosed by Scheit in his text *Nucleotide Analogs*, a Wiley-Interscience Publication, John Wiley and Sons.

The need for additional compounds that can be used to treat acute cerebral malaria and other diseases that mediate the production of TNF-$\alpha$, such as endotoxin shock, is great because the TNF-$\alpha$ produced is highly toxic. For example, only low levels of LPS are needed for mortality, i.e. the $LD_{50}$ for the lipopolysaccharide in sheep is about 10-20 µg/kg (intravenous), while in mice it is about 5 mg/kg. In sheep (and probably also in humans) lipopolysaccharide causes death by promoting the release of mediators that trigger pulmonary hypertension, pulmonary edema, and peripheral vascular collapse. Death usually occurs within 8 to 48 hours after injection of lipopolysaccharide or lipid A. Occasionally, death will occur at 1-2 weeks. This is usually the result of disseminated intravascular coagulopathy leading to renal cortical necrosis and uremic death.

Previous work on the lethal endotoxicity of LPS showed that only limited prevention of the complications of injection of this material could be achieved through the administration of glucocorticoids, prostaglandins, naloxone, pressors, fluid replacement therapy or anti-LPS antibodies. In addition, all existing therapies against LPS lethality are dependent upon their being given prior to or very shortly after the administration of the LPS challenge.

Furthermore, protection with compounds, such as 2-MeS-ATP, might be obtained even after the signs and symptoms of endotoxemia had been developed. This is an extremely important therapeutic consideration, since the signs and symptoms of a disease must almost always manifest before therapy is initiated. Although the mechanism(s) by which protective compounds inhibit LPS-inducible GTPase activity in the assay remain unknown, the data fit best for agents interrupting a signal transduction pathway involving purinoreceptors that are linked to an endotoxin-responsive G-protein (i.e., GTPase) that ultimately leads to the release of IL-1 and TNF by macrophages.

The pretreatment of mammals, such as humans, sheep or mice, with a compound of Formula I which can block adenine nucleotide-stimulated GTPase activity should make the mammal resistant to the lethal effects of Gram-negative endotoxin.

We also envision that treatment of a mammal after the symptoms of endotoxin shock appear will lessen disease symptoms. Of note, current therapies are aimed at killing the gram negative bacteria (antibiotics) and at neutralizing circulating endotoxin (anti-endotoxin antibodies). However, these therapies have the disadvantages of releasing more endotoxin and having no effect on endotoxin already internalized into cells. This last disadvantage is clinically very relevant because the signs and symptoms of endotoxemia are often not manifest until 1.5-3 hours after the endotoxin is released into the patient, thus rendering anti-endotoxin antibodies less effective. The apparent antagonism between the compounds identified as GTPase inhibitors and endotoxin can have useful applications in clinical situations and disease states that are caused by endotoxin, such as Gram-negative sepsis following surgery in humans and animals, bovine or porcine mastitis, and other endotoxin-related veterinary diseases listed in Tables 2 and 3.

Although the foregoing tests all involved the use of the two compounds, the administration of other compounds of Formula I which are identified as inhibiting GTPase, also can be useful to ameliorate the adverse effects of TNF-$\alpha$ which is produced by the interaction of many disease agents with macrophages and T-cells.

In the method of the present invention, the compounds of Formula I may be introduced into the circulation of an animal by oral, intravenous, intraperitoneal or intramuscular routes. When thus employed, the compounds may be administered in the form of parenteral solutions containing the selected protective compound, in a sterile liquid suitable for intravenous or other administration. The exact route, dose, and administration interval of the active compounds will vary with the size and weight of the animal, and the species, and the desired level of protection. However, in general the dosage will be similar to those for 2-chloro-ATP and 2-methylthio-ATP which are about 1 mg/kg to about 50 mg/kg.

Table 1

Pet Animal and Livestock Pathophysiological Entities in Which the Adverse Effects of TNF-$\alpha$ Can Be Prevented or Treated by Administration of Compounds Which Inhibit GTPase are the following:

Mammalian

Gastritis

Digestive disorders of the rumen including
  Bloat
  Simple indigestion
  Grain overload Abomasal disorders
  Displacement/torsion of the abomasum
  Impaction of the abomasum Edema disease of swine Colibacillosis of weaned pigs Enteritis of small and large animals Small intestinal obstruction Colon impaction of small animals Intussusceptions Intestinal torsion and volvulus Impaction of the large intestine Intestinal foreign bodies Intestinal incarceration Colitis Colic in horses Salmonellosis/typhoid fever Colibacillosis
Diarrhea of newborn animals
Chronic diarrhea
Toxicosis of chemical and plant origins
Gastrointestinal parasites including coccidiosis and sarcosporidiosis
Malabosorbtion syndrome
Hemorrhagic bowel syndrome
All other syndromes which cause loss of gastrointestinal homogeneity such as abrupt changes in diet or feeding regimen in mammalian species
Infectious necrotic hepatitis
Bacillary hemoglobinuria
Hepatitis of parasitic etiology
Hepatic distomatosis
  Chemical hepatosis from protein deficiencies, vitamin E deficiency, pyrrolizidine alkaloids, from parasites during migrations, infectious and pyogenic diseases, metabolic diseases, copper poisonings
Avian syndromes
Enteritis of infectious or nutritional origin;
  infectious etiology is intended to include bacterial, viral and parasitic etiologies.
Hepatitis of infectious or parasitic etiologies
Coccidiosis, hexamitiasis, histomoniasis Table 2

Human Diseases in Which the Adverse Effects of TNF-α Can Be Prevented or Treated by the Administration of Compounds Which Inhibit GTPase are the following:

(1) Gram-negative sepsis
(2) Endotoxemia from burn wounds, pyelonephritis, peritonitis, cellulitis, abscess, prostatitis, genitourinary tract infections, mastitis, pneumonia, empyema, cholecystitis, bacterial hepatitis, meningococcemia, gonococcemia, colitis, toxic megacolon, meningitis, etc.
(3) Loss of G.I. mucosal barrier, e.g. trauma, drug-induced mucositis.

Table 3

Other diseases in which the method of the present invention can be useful are:
Pancreatitic
Myocardial infarction
Crush Trauma
Burns (chemical and thermal)
Vasculitis
Drug toxicities involving macrophage activation
Toxic shock syndrome
Enterotoxin
Overwhelming Viremia
Viral pneumonia
Immune complex diseases
Aspiration pneumonia
Drowning
Inhaled toxins or irritants
Shock lung
Reperfusion injuries It will be apparent to those skilled in the art that a number of changes and modifications can be made without departing from the spirit and scope of the present invention. Therefore, it is intended that the invention only be limited by the claims.

References

1. Grau et al, Proc Natl Acad Sci, 86, 5572–5574 (1989)
2. Grau et al, J Exp Med, 168, 1499–1504 (1988)
3. Grau et al, Science, 237, 1210–1212 (1987)
4. Howard and Gilladoga, Blood, 74, 2603–2618 (1989)
5. Grau et al, Immunol Rev, 112, 49–70, (1989)
6. Clark et al, Tran Roy Soc Trop Med Hyg, 83,436–440 (1969)
7. Rest, JR, Tran Roy Soc Trop Med Hyg, V6, 410–415 (1982)
8. Graninger et al, J Infect Dis, 164, 829 (1991)
9. Weston et al, Lancet, ii:602, 609 (1982)
10. Kremsner et al, J Infect Dis, 164, 605–608 (1991)
11. Sliwa et al, Infect Immun, 59, 3846–3848 (1991)
12. Bertics et al, Bacterial endotoxin: Recognition and Effector Mechanisms, eds. Levin et al (Elsevier Science Publishers B.V.) pp 233–241
13. Proctor et al, Proc. Natl. Acad. Sci. U.S.A., Vol. 91 pp 6017–6020 (1994)

The embodiments of the invention in which an exclusive property or privilege is claimed are the following:

1. A method of reducing TNF-alpha in a mammal with cerebral malaria comprising administering to said mammal a safe and therapeutically effective amount of a compound of Formula I:

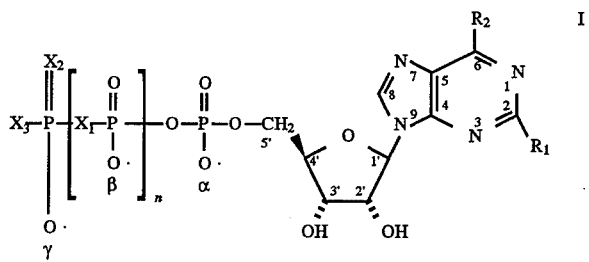

in which $X_1$ is a hydroxylation preventing group selected from the group consisting of —O—, —NH— and —CH$_2$—; $X_2$ is =O; $X_3$ is —OH; $R_1$ is an electron withdrawing group selected from the group consisting of a alkylthio of 1 to 4 carbon atoms, chloro, fluoro and trichloromethyl; $R_2$ is —NH$_2$, —NH(CH$_3$), or —N(CH$_3$)$_2$ ; and n is 0 or 1.

2. A method of claim 1 in which $R_1$ is chloro.
3. A method of claim 1 in which $R_1$ is methylthio.
4. A method of claim 1 in which the compound administered is 2-methylthio-ATP.
5. A method of claim 1 in which the compound administered is 2-chloro-ATP.

* * * * *

UNITED STATES PATENT AND TRADEMARK OFFICE
CERTIFICATE OF CORRECTION

Patent No.    : 5,624,913
Dated         : April 29, 1997
Inventor(s)   : Richard A. Proctor and Paul J. Bertics It is certified that error appears in the above-identified patent and that said Letters Patent is hereby corrected as shown below:

On the title page:

Item: [*] Notice: "The term of this patent shall not extend beyond the expiration date of Pat. No. 5,492,899." should be --The term of this patent shall not extend beyond the expiration date of Pat. No. 5,492,898.--

Signed and Sealed this

Twelfth Day of August, 1997

Attest:

BRUCE LEHMAN

Attesting Officer          Commissioner of Patents and Trademarks